US012599285B2

(12) United States Patent
Baras et al.

(10) Patent No.: US 12,599,285 B2
(45) Date of Patent: Apr. 14, 2026

(54) ANALYSIS OF IN-VIVO IMAGES USING CONNECTED GRAPH COMPONENTS

(71) Applicant: Given Imaging LTD, Yoqneam (IL)

(72) Inventors: Dorit Baras, Haifa (IL); Tomer Goldstein, Ramat HaSharon (IL); Gal Shenker, Nahariya (IL)

(73) Assignee: GIVEN IMAGING LTD., Yoqneam (IL)

( * ) Notice: Subject to any disclaimer, the term of this patent is extended or adjusted under 35 U.S.C. 154(b) by 366 days.

(21) Appl. No.: 18/206,868

(22) Filed: Jun. 7, 2023

(65) Prior Publication Data

US 2023/0397794 A1     Dec. 14, 2023

Related U.S. Application Data

(60) Provisional application No. 63/351,875, filed on Jun. 14, 2022.

(51) Int. Cl.
A61B 1/00 (2006.01)
A61B 1/04 (2006.01)
(Continued)

(52) U.S. Cl.
CPC ........ A61B 1/000096 (2022.02); A61B 1/041 (2013.01); A61B 1/31 (2013.01);
(Continued)

(58) Field of Classification Search
CPC ..... A61B 1/000096; A61B 1/041; A61B 1/31; A61B 1/000094; G06T 7/0014;
(Continued)

(56) References Cited

U.S. PATENT DOCUMENTS

2020/0387706 A1* 12/2020 Zur ........................ G06T 7/0012

FOREIGN PATENT DOCUMENTS

| WO | 2020079696 A1 | 4/2020 |
| WO | 2020236683 A1 | 11/2020 |
| WO | 2022049577 A1 | 3/2022 |

OTHER PUBLICATIONS

Ahmedt-Aristizabal et al, "A survey on graph-based deep learning for computational histopathology", Computerized Medical Imaging and Graphics, vol. 95, 2022, 102027, ISSN 0895-6111, https://doi.org/10.1016/j.compmedimag.2021.102027. https://www.sciencedirect.com/science/article/pii/S0895611121001762 (Year: 2022).*

(Continued)

*Primary Examiner* — Matthew C Bella
*Assistant Examiner* — Andrew B. Jones
(74) *Attorney, Agent, or Firm* — Carter, DeLuca & Farrell LLP

(57) ABSTRACT

A system includes at least one processor, and at least one memory storing instructions. The instructions, when executed by the processor(s), cause the system to: access a in-vivo images captured by a capsule endoscope where the in-vivo images are designated as containing a pathology indicator; form a connected graph component based on the in-vivo images where the connected graph component includes at least two images of the in-vivo images connected based on at least one indication that the at least two images contain the same occurrence of the pathology indicator; process the connected graph component with a machine learning model to provide a score indicative of whether the at least two images contain the same occurrence of the pathology indicator; and associate the score with the at least two images for presentation to a reviewer of the at least two images.

20 Claims, 9 Drawing Sheets

(51) Int. Cl.
    *A61B 1/31*        (2006.01)
    *G06T 7/00*       (2017.01)
(52) U.S. Cl.
    CPC ........ *G06T 7/0014* (2013.01); *G06T 2200/24*
        (2013.01); *G06T 2207/10068* (2013.01); *G06T*
           *2207/20072* (2013.01); *G06T 2207/20084*
           (2013.01); *G06T 2207/30092* (2013.01)
(58) Field of Classification Search
    CPC ....... G06T 2200/24; G06T 2207/10068; G06T
           2207/20072; G06T 2207/20084; G06T
              2207/30092; G06T 7/0016; G06T
                 2207/20081; G06T 2207/30032
    See application file for complete search history.

(56)             References Cited

OTHER PUBLICATIONS

W. Du et al., "Review on the Applications of Deep Learning in the Analysis of Gastrointestinal Endoscopy Images," in IEEE Access, vol. 7, pp. 142053-142069, 2019, doi: 10.1109/ACCESS.2019. 2944676. https://ieeexplore.ieee.org/document/8853349 (Year: 2019).*

* cited by examiner

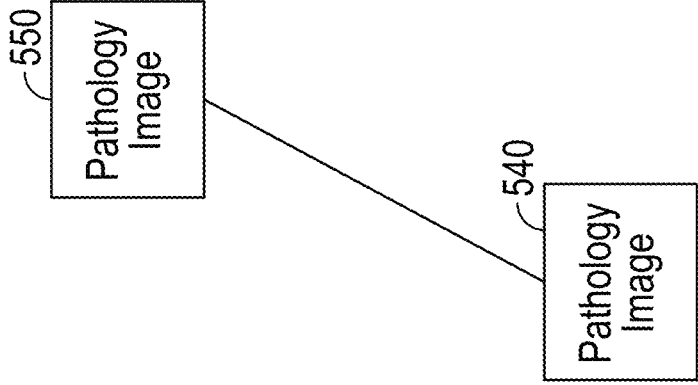
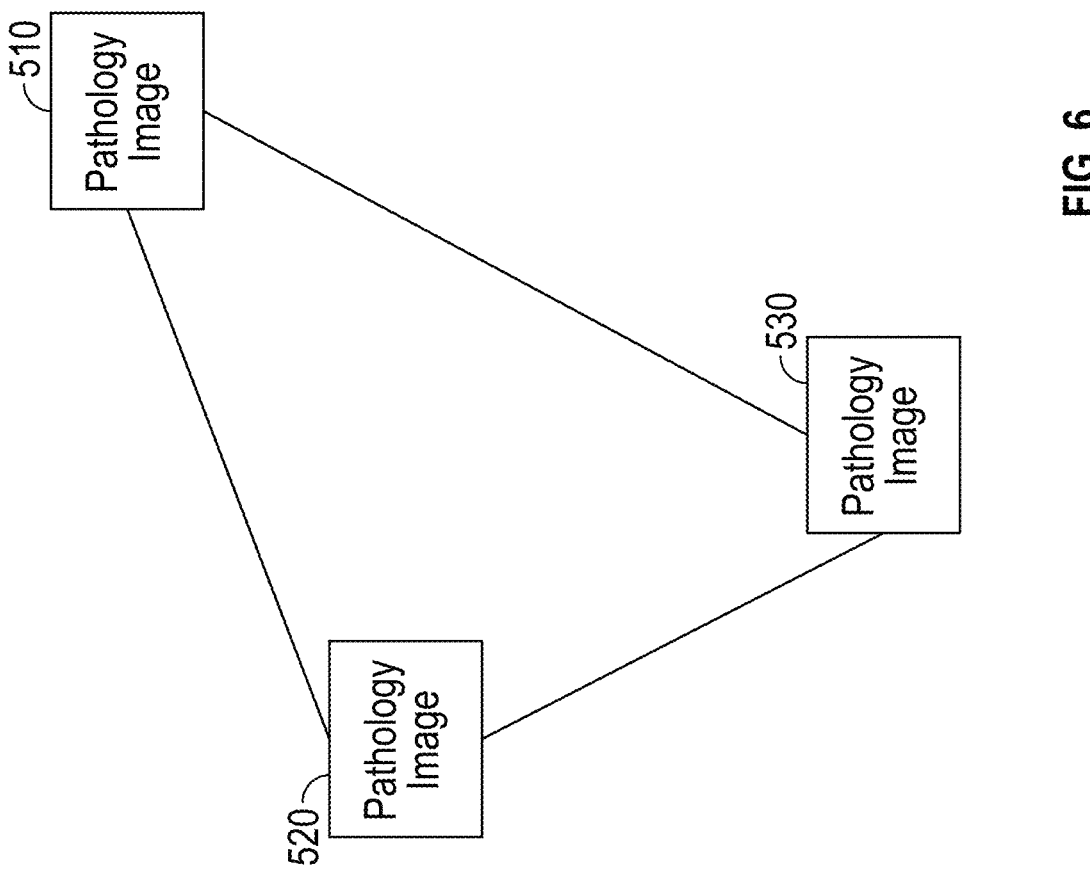
FIG. 6

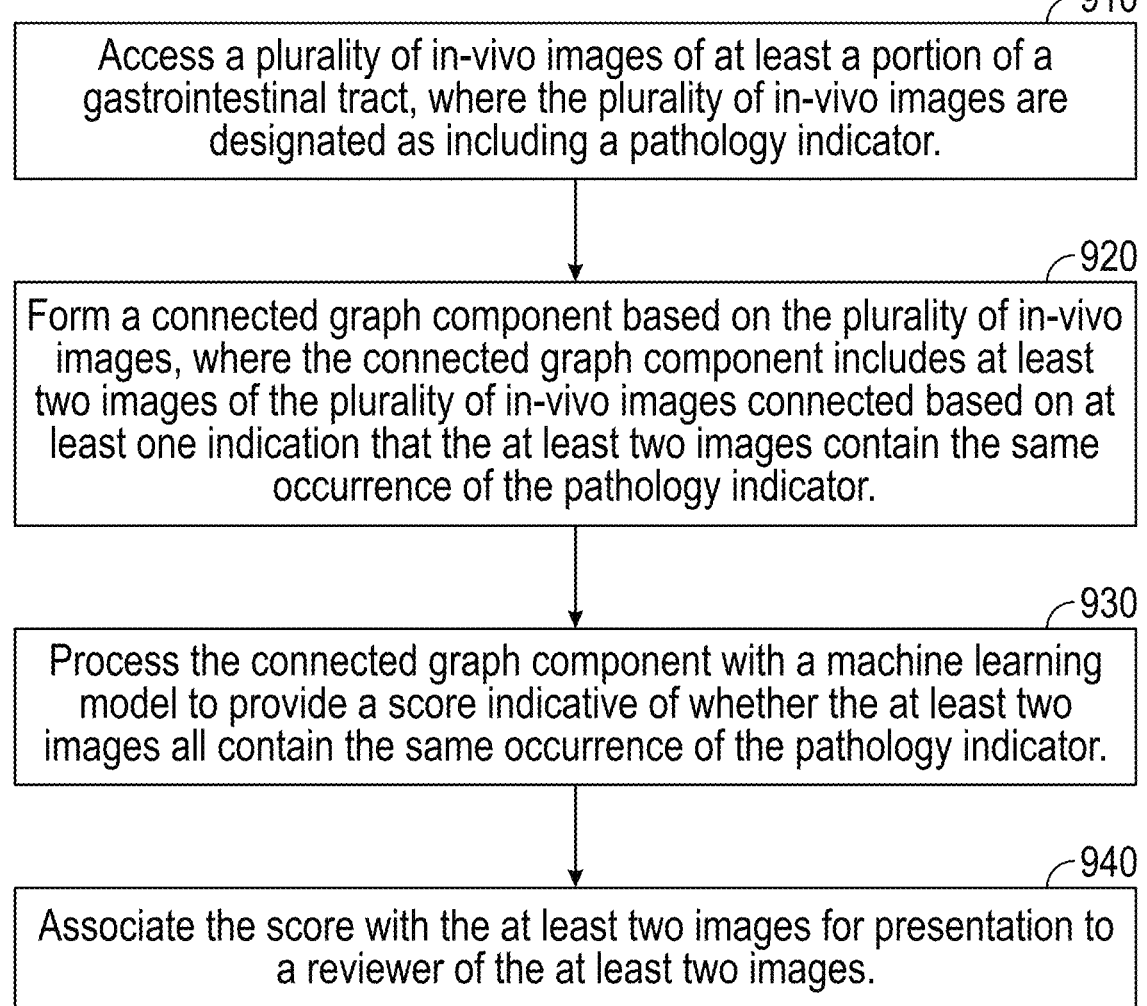

910

Access a plurality of in-vivo images of at least a portion of a gastrointestinal tract, where the plurality of in-vivo images are designated as including a pathology indicator.

920

Form a connected graph component based on the plurality of in-vivo images, where the connected graph component includes at least two images of the plurality of in-vivo images connected based on at least one indication that the at least two images contain the same occurrence of the pathology indicator.

930

Process the connected graph component with a machine learning model to provide a score indicative of whether the at least two images all contain the same occurrence of the pathology indicator.

940

Associate the score with the at least two images for presentation to a reviewer of the at least two images.

FIG. 9

ANALYSIS OF IN-VIVO IMAGES USING CONNECTED GRAPH COMPONENTS

CROSS-REFERENCE TO RELATED APPLICATIONS

This application claims the benefit of U.S. Provisional Application Ser. No. 63/351,875, filed Jun. 14, 2022, the entire contents of which are hereby incorporated by reference herein.

TECHNICAL FIELD

The present disclosure relates image analysis of in-vivo images of a gastrointestinal tract (GIT) and, more particularly, to analyzing in-vivo images to identify pathology indicators.

BACKGROUND

Capsule endoscopy (CE) allows examining of a GIT endoscopically. There are capsule endoscopy systems and methods that are aimed at examining a specific portion of the GIT, such as the small bowel (SB) or the colon. CE is a non-invasive procedure which does not require the patient to be admitted to a hospital, and the patient can continue most daily activities while the capsule is in his body.

For a typical CE procedure, the patient is referred to a procedure by a physician. The patient then arrives at a medical facility (e.g., a clinic or a hospital), to perform the procedure. The capsule, which is about the size of a multivitamin, is swallowed by the patient under the supervision of a health professional (e.g., a nurse or a physician) at the medical facility and the patient is provided with a wearable device, e.g., a sensor belt having a recorder in a pouch and a strap to be placed around the patient's shoulder. The wearable device typically includes a storage device. The patient may be given guidance and/or instructions and then released to his daily activities.

The capsule captures images as it travels naturally through the GIT. Images and additional data (e.g., metadata) are then transmitted to the recorder that is worn by the patient. The capsule is typically disposable and passes naturally with a bowel movement. The procedure data (e.g., the captured images or a portion of them and additional metadata) is stored on the storage device of the wearable device.

The procedure data is uploaded from the wearable device to a computing system, which has an engine software stored thereon. The procedure data is then processed by the engine to generate a compiled study. Typically, the number of images in the procedure data to be processed is of the order of tens of thousands, and the generated study typically includes thousands of images.

A reader (which may be the procedure supervising physician, a dedicated physician or the referring physician) may access the study via a reader application. The reader then reviews the study, evaluates the procedure, and provides input via the reader application. Since the reader needs to review thousands of images, the reading time of a study may usually take between half an hour to an hour on average and the reading task may be tiresome. A report is then generated by the reader application based on the compiled study and the reader's input. On average, it may take an hour to generate a report. The report may include, for example, images of interest, e.g., images which are identified as including pathologies, selected by the reader; evaluation or diagnosis of the patient's medical condition based on the procedure's data (i.e., the study) and/or recommendations for follow up and/or treatment provided by the reader. The report may be then forwarded to the referring physician. The referring physician may decide on a required follow up or treatment based on the report.

SUMMARY

The present disclosure relates to analyzing in-vivo images to identify pathology indicators, such as colon polyps or other indicator. Aspects of the present disclosure relate to identifying sets of in-vivo images which may contain the same occurrence of a pathology indicator (e.g., the same polyp, the same ulcer, etc.). Aspects of the present disclosure relate to identifying sets of in-vivo images which contain a pathology indicator but which may contain different occurrences of a pathology indicator (e.g., distinct polyps, distinct ulcers, etc.). To the extent consistent, any or all of the aspects, embodiments, and examples detailed herein may be used in conjunction with any or all of the other aspects or embodiments detailed herein.

In accordance with aspects of the present disclosure, a system for analyzing images includes: at least one processor, and at least one memory storing instructions. The instructions, when executed by the at least one processor, cause the system to: access a plurality of in-vivo images of at least a portion of a gastrointestinal tract where the plurality of in-vivo images are designated as containing a pathology indicator; form a connected graph component based on the plurality of in-vivo images where the connected graph component includes at least two images of the plurality of in-vivo images connected based on at least one indication that the at least two images contain the same occurrence of the pathology indicator; process the connected graph component with a machine learning model to provide a score indicative of whether the at least two images contain the same occurrence of the pathology indicator; and associate the score with the at least two images for presentation to a reviewer of the at least two images. In various embodiments, the at least one indication that the at least two images contain the same occurrence of the pathology indicator includes a similarity score for each connection in the connected graph component.

In various embodiments of the system, in forming the connected graph component based on the plurality of in-vivo images, the instructions, when executed by the at least one processor, cause the system to, for each image pair of the plurality of in-vivo images: analyze whether both images of the respective image pair contain the same occurrence of the pathology indicator, and based on the analysis indicating that both images of the respective image pair contain the same occurrence of the pathology indicator, designate both images of the respective image pair as graph nodes and connect the graph nodes by an edge. Further, the instructions cause the system to select a group of graph nodes which are connected by one or more edges as the connected graph component.

In various embodiments of the system, in analyzing whether both images of the respective image pair contain the same occurrence of the pathology indicator, the instructions, when executed by the at least one processor, cause the system to: process both images of the respective image pair by a triplet-loss network to provide an output score; and provide an indication of whether both images of the respective image pair contain the same occurrence of the pathology indicator based on comparing the output score to a predetermined score threshold. In various embodiments, the images may be processed by a technique other than a triplet-loss network.

In various embodiments of the system, the instructions, when executed by the at least one processor, further cause the system to determine at least one graph characteristic of the connected graph component, where processing the connected graph component with the machine learning model includes inputting the at least one graph characteristic to the machine learning model.

In various embodiments of the system, the at least one graph characteristic includes at least one of: number of nodes of the connected graph component, number of edges of the connected graph component, ratio of nodes to edges in the connected graph component, or ratio of edges to nodes in the connected graph component.

In various embodiments of the system, the instructions, when executed by the at least one processor, further cause the system to communicate a user interface to a device of the reviewer, where the user interface includes a presentation of the at least two images and of the score associated with the at least two images.

In various embodiments of the system, the user interface further includes, based on a value of the score associated with the at least two images, one of: an indication that the at least two images may contain the same occurrence of the pathology indicator, or an indication that the at least two images may contain different occurrences of the pathology indicator.

In accordance with aspects of the present disclosure, a method for analyzing images includes: accessing a plurality of in-vivo images of at least a portion of a gastrointestinal tract where the plurality of in-vivo images are designated as containing a pathology indicator; forming a connected graph component based on the plurality of in-vivo images where the connected graph component includes at least two images of the plurality of in-vivo images connected based on at least one indication that the at least two images contain the same occurrence of the pathology indicator; processing the connected graph component with a machine learning model to provide a score indicative of whether the at least two images contain the same occurrence of the pathology indicator; and associating the score with the at least two images for presentation to a reviewer of the at least two images. In various embodiments, the at least one indication that the at least two images contain the same occurrence of the pathology indicator includes a similarity score for each connection in the connected graph component.

In various embodiments of the method, forming the connected graph component based on the plurality of in-vivo images includes, for each image pair of the plurality of in-vivo images: analyzing whether both images of the respective image pair contain the same occurrence of the pathology indicator, and based on the analysis indicating that both images of the respective image pair contain the same occurrence of the pathology indicator, designating both images of the respective image pair as graph nodes and connecting the graph nodes by an edge. The method includes selecting a group of graph nodes which are connected by one or more edges as the connected graph component.

In various embodiments of the method, analyzing whether both images of the respective image pair contain the same occurrence of the pathology indicator includes: processing both images of the respective image pair by a triplet-loss network to provide an output score, and providing an indication of whether both images of the respective image pair contain the same occurrence of the pathology indicator based on comparing the output score to a predetermined score threshold. In various embodiments, the images may be processed by a technique other than a triplet-loss network.

In various embodiments of the method, the method includes determining at least one graph characteristic of the connected graph component, where processing the connected graph component with the machine learning model includes inputting the at least one graph characteristic to the machine learning model.

In various embodiments of the method, the at least one graph characteristic includes at least one of: number of nodes of the connected graph component, number of edges of the connected graph component, ratio of nodes to edges in the connected graph component, or ratio of edges to nodes in the connected graph component.

In various embodiments of the method, the method includes communicating a user interface to a device of the reviewer, where the user interface includes a presentation of the at least two images and of the score associated with the at least two images.

In various embodiments of the method, the user interface further includes, based on a value of the score associated with the at least two images, one of: an indication that the at least two images may contain the same occurrence of the pathology indicator, or an indication that the at least two images contain different occurrences of the pathology indicator.

In accordance with aspects of the present disclosure, a processor-readable medium stores instructions which, when executed by at least one processor of a system, cause the system to: access a plurality of in-vivo images of at least a portion of a gastrointestinal tract where the plurality of in-vivo images are designated as containing a pathology indicator; form a connected graph component based on the plurality of in-vivo images where the connected graph component includes at least two images of the plurality of in-vivo images connected based on at least one indication that the at least two images contain the same occurrence of the pathology indicator; process the connected graph component with a machine learning model to provide a score indicative of whether the at least two images contain the same occurrence of the pathology indicator; and associate the score with the at least two images for presentation to a reviewer of the at least two images. In various embodiments, the at least one indication that the at least two images contain the same occurrence of the pathology indicator includes a similarity score for each connection in the connected graph component.

In various embodiments of the processor-readable medium, in forming the connected graph component based on the plurality of in-vivo images, the instructions, when executed by the at least one processor, cause the system to, for each image pair of the plurality of in-vivo images: analyze whether both images of the respective image pair contain the same occurrence of the pathology indicator, and based on the analysis indicating that both images of the respective image pair contain the same occurrence of the pathology indicator, designate both images of the respective image pair as graph nodes and connect the graph nodes by an edge. The instructions further cause the system to select a group of graph nodes which are connected by one or more edges as the connected graph component.

In various embodiments of the processor-readable medium, in analyzing whether both images of the respective image pair contain the same occurrence of the pathology indicator, the instructions, when executed by the at least one processor, cause the system to process both images of the respective image pair by a triplet-loss network to provide an output score, and provide an indication of whether both images of the respective image pair contain the same occurrence of the pathology indicator based on comparing the output score to a predetermined score threshold. In various embodiments, the images may be processed by a technique other than a triplet-loss network.

In various embodiments of the processor-readable medium, the instructions, when executed by the at least one processor, further cause the system to determine at least one graph characteristic of the connected graph component, where processing the connected graph component with the machine learning model includes inputting the at least one graph characteristic to the machine learning model.

In various embodiments of the processor-readable medium, the at least one graph characteristic includes at least one of: number of nodes of the connected graph component, number of edges of the connected graph component, ratio of nodes to edges in the connected graph component, or ratio of edges to nodes in the connected graph component.

In various embodiments of the processor-readable medium, the instructions, when executed by the at least one processor, further cause the system to communicate a user interface to a device of the reviewer, where the user interface includes a presentation of the at least two images and of the score associated with the at least two images.

Further details and aspects of exemplary embodiments of the present disclosure are described in more detail below with reference to the appended figures.

BRIEF DESCRIPTION OF THE DRAWINGS

A better understanding of the features and advantages of the disclosed technology will be obtained by reference to the following detailed description that sets forth illustrative embodiments, in which the principles of the technology are utilized, and the accompanying drawings of which:

FIG. 6 is a diagram of two exemplary connected graph components, in accordance with aspects of the disclosure;

FIG. 9 is a flow diagram of an exemplary image processing operation, in accordance with aspects of the disclosure.

DETAILED DESCRIPTION

Figure 1:
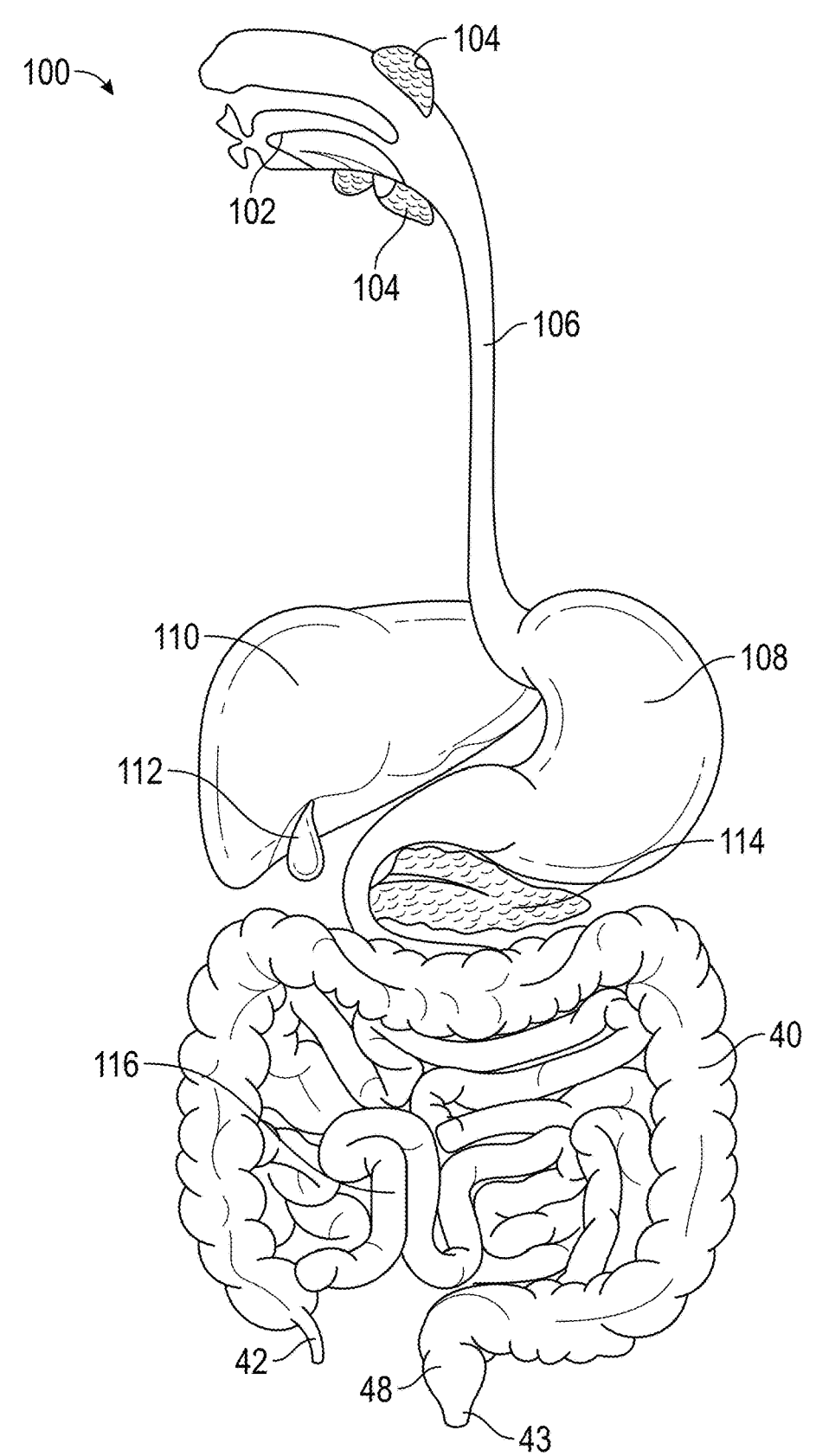
FIG. 1 is a diagram of a gastrointestinal tract (GIT)

The present disclosure relates to analyzing in-vivo images to identify pathology indicators, such as colon polyps or other indicator. Aspects of the present disclosure relate to identifying sets of in-vivo images which may contain the same occurrence of a pathology indicator (e.g., the same polyp, the same ulcer, etc.). Aspects of the present disclosure relate to identifying sets of in-vivo images which contain a pathology indicator but which may contain different occurrences of a pathology indicator (e.g., distinct polyps, distinct ulcers, etc.). As used herein, the term "pathology indicator" means and includes an indicator of a pathology of a GIT, such as internal bleeding, a foreign body or material, parasites, an indicator of potential cancerous growth (such as a colon polyp), ulcer, lesion, angioectasia, diverticulum, or mass, among other things.

An in-vivo imaging device, such has a capsule endoscope, can move back and forth during a procedure, so the same tissue or pathology indicator (e.g., a polyp) can be seen from different angles and distances. By identifying images containing the same occurrence of a pathology indicator or by noting that images contain different occurrences of a pathology indicator, more information may be provided to reviewers for evaluating the images to assess health of the GIT.

In the following detailed description, specific details are set forth in order to provide a thorough understanding of the disclosure. However, it will be understood by those skilled in the art that the disclosure may be practiced without these specific details. In other instances, well-known methods, procedures, and components have not been described in detail so as not to obscure the present disclosure. Some features or elements described with respect to one system may be combined with features or elements described with respect to other systems. For the sake of clarity, discussion of same or similar features or elements may not be repeated.

To the extent consistent, any or all of the aspects, embodiments, and examples detailed herein may be used in conjunction with any or all of the other aspects or embodiments detailed herein.

Although the disclosure is not limited in this regard, discussions utilizing terms such as, for example, "processing," "computing," "calculating," "determining," "establishing," "analyzing," "checking," or the like, may refer to operation(s) and/or process(es) of a processor, a computing platform, a computing system, or other electronic computing device, that manipulates and/or transforms data represented as physical (e.g., electronic) quantities within computing registers and/or memories into other data similarly represented as physical quantities within the computing registers and/or memories or other non-transitory information storage medium that may store instructions to perform operations and/or processes.

Although the disclosure is not limited in this regard, the terms "plurality" and "a plurality" as used herein may include, for example, "multiple" or "two or more." The terms "plurality" or "a plurality" may be used throughout the specification to describe two or more components, devices, elements, units, parameters, or the like.

As used herein, the term "exemplary" means "an example" and is not intended to mean preferred. Unless explicitly stated, the methods described herein are not constrained to a particular order or sequence. Additionally, some of the described methods or elements thereof can occur or be performed simultaneously, at the same point in time, or concurrently.

Depending on the context, the terms "GIT" may mean a portion of the GIT and/or the entirety of a GIT. Thus, disclosures relating to a GIT may apply to a portion of the GIT and/or the entirety of a GIT.

The terms "image" and "frame" may each refer to or include the other and may be used interchangeably in the present disclosure to refer to a single capture by an imaging device. For convenience, the term "image" may be used more frequently in the present disclosure, but it will be understood that references to an image shall apply to a frame as well. As used herein, a "set" of images means and includes any collection of images, including images that may be ordered, unordered, consecutive, and/or non-consecutive.

The present disclosure may refer to images that are "designated" or "indicated" as containing a pathology indicator and/or may refer to information, data, or scores "indicative" of an image containing the same occurrence or different occurrences of a pathology indicator. Such descriptions do not mean and are not intended to mean that an image definitely contains a pathology indicator (e.g., a polyp) or definitely contains the same occurrence or different occurrences of a pathology indicator (e.g., the same polyp). Rather, such descriptions mean and are intended to mean that an image has such a designation or indication (whether or not such a designation or indication is actually true).

The term "machine learning" means and includes any technique which analyzes existing data to learn a model between inputs and outputs in the existing data. The term "machine learning model" means and includes any implementation of the learned model, in software and/or hardware, that can receive new input data and that can predict/infer output data by applying the learned model to the new input data. Machine learning may include supervised learning and unsupervised learning, among other things. Examples of machine learning models include, without limitation, deep learning neural networks and support vector machines, among other things.

The term "connected graph component" means and includes any portion of a graph that contains vertices and edges in which every vertex is reachable from any other vertex by traversing the edges.

Referring to FIG. 1, an illustration of a gastrointestinal tract (GIT) 100 is shown. The GIT 100 is an organ system within humans and animals. The GIT 100 generally includes a mouth 102 for taking in sustenance, salivary glands 104 for producing saliva, an esophagus 106 through which food passes aided by contractions, a stomach 108 to secret enzymes and stomach acid to aid in digesting food, a liver 110, a gall bladder 112, a pancreas 114, a small intestine/small bowel 116 ("SB") for the absorption of nutrients, and a colon 40 (e.g., large intestine) for storing water and waste material as feces prior to defecation. The colon 40 generally includes an appendix 42, a rectum 48, and an anus 43. Food taken in through the mouth is digested by the GIT to take in nutrients and the remaining waste is expelled as feces through the anus 43.

The type of procedure performed may determine which portion of the GIT 100 is the portion of interest. Examples of types of procedures performed include, without limitation, a procedure aimed to specifically exhibit or check the small bowel, a procedure aimed to specifically exhibit or check the colon, a procedure aimed to specifically exhibit or check the colon and the small bowel, or a procedure to exhibit or check the entire GIT: esophagus, stomach, SB, and colon, among other possibilities.

Figure 2:
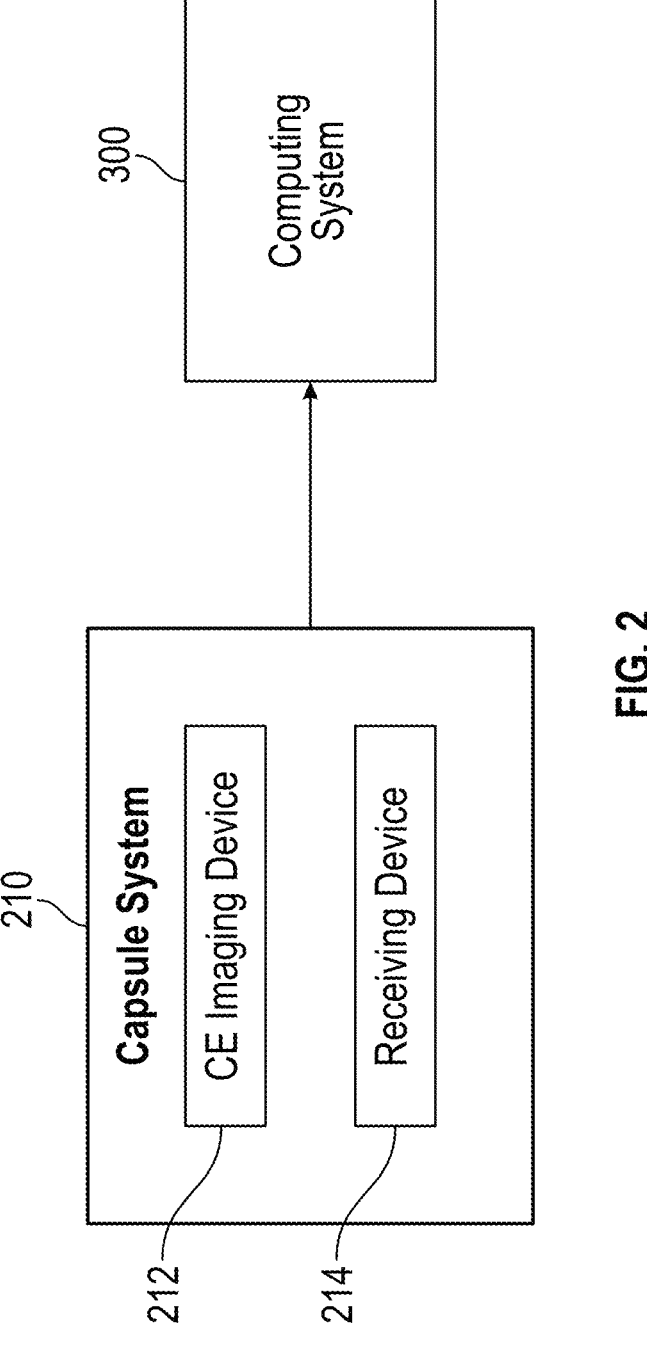
FIG. 2 is a block diagram of an exemplary system for analyzing medical images captured in-vivo via a Capsule Endoscopy (CE) procedure, in accordance with aspects of the disclosure.

FIG. 2 shows a block diagram of a system for analyzing medical images captured in-vivo via a capsule endoscopy ("CE") procedure. The system generally includes a capsule system 210 configured to capture images of the GIT and a computing system 300 (e.g., local system and/or cloud system) configured to process the captured images.

The capsule system 210 may include a swallowable CE imaging device 212 (e.g., a capsule) configured to capture images of the GIT as the CE imaging device 212 travels through the GIT. The images may be stored on the CE imaging device 212 and/or transmitted to a receiving device 214, typically via an antenna. In some capsule systems 210, the receiving device 214 may be located on the patient who swallowed the CE imaging device 212 and may, for example, take the form of a belt worn by the patient or a patch secured to the patient.

The capsule system 210 may be communicatively coupled with the computing system 300 and can communicate captured images to the computing system 300. The computing system 300 may process the received images using image processing technologies, machine learning technologies, and/or signal processing technologies, among other technologies. The computing system 300 may include local computing devices that are local to the patient and/or local to the patient's treatment facility, a cloud computing platform that is provided by cloud services, or a combination of local computing devices and a cloud computing platform.

In the case where the computing system 300 includes a cloud computing platform, the images captured by the capsule system 210 may be transmitted to the cloud computing platform. In various embodiments, the images can be transmitted by or via the receiving device 214 worn or carried by the patient. In various embodiments, the images can be transmitted via the patient's smartphone or via any other device which is connected to the Internet and which may be coupled with the CE imaging device 212 or the receiving device 214.

Figure 3:
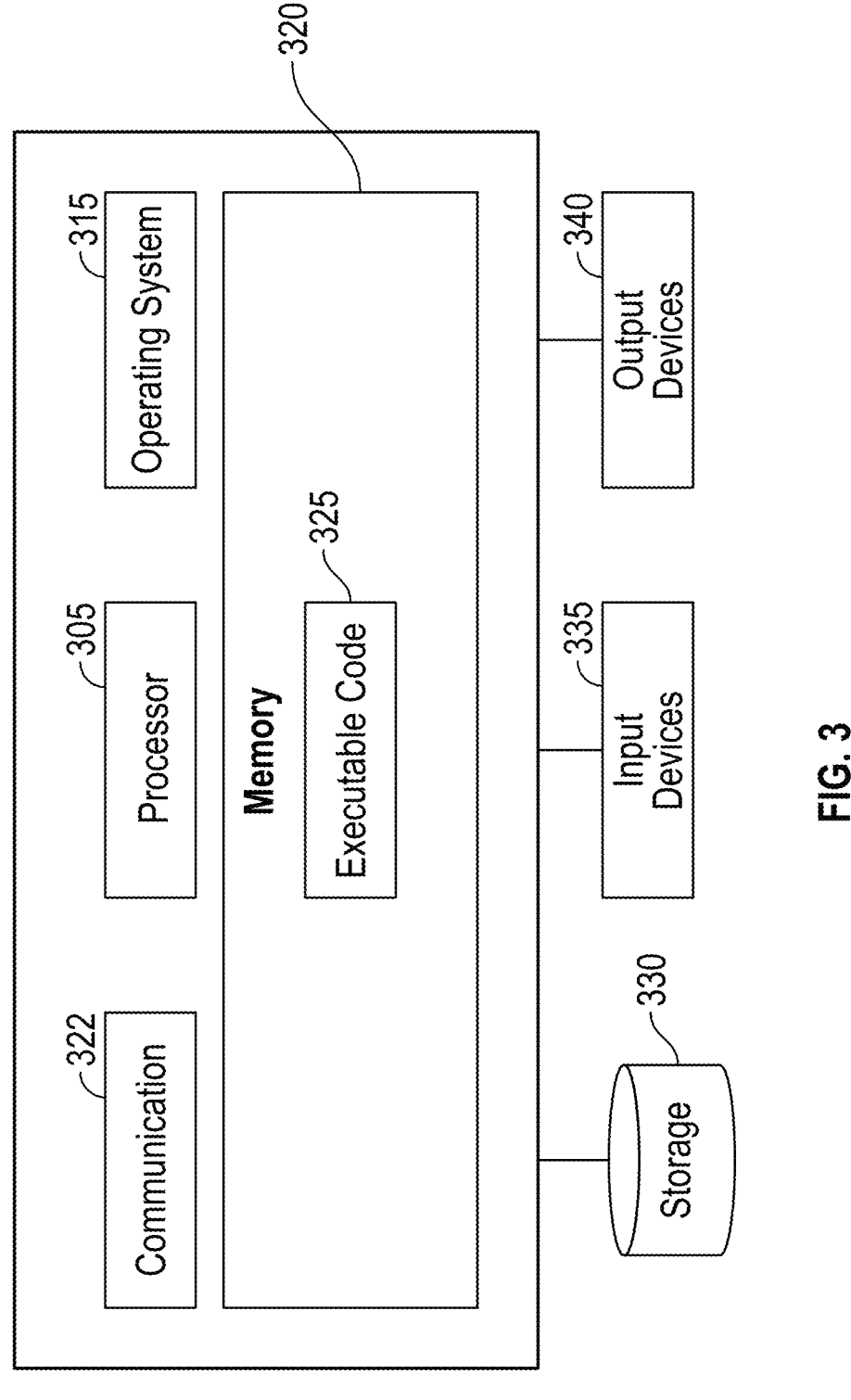
FIG. 3 is a block diagram of an exemplary computing system, in accordance with aspects of the disclosure.

FIG. 3 shows a block diagram of example components of the computing system 300 of FIG. 2. The computing system 300 includes a processor 305, an operating system 315, a memory 320, a communication device 322, a storage 330, input devices 335, and output devices 340. The communication device 322 of the computing system 300 may allow communications with other systems or devices via a wired network (e.g., Ethernet) and/or a wireless network (e.g., Wi-Fi, cellular network, etc.).

The processor 305 may be or may include one or more central processing units (CPU), graphics processing unit (GPU), controllers, microcontrollers, microprocessors, and/or other computational devices. The operating system 315 may be or may include any code segment designed and/or configured to perform tasks involving coordination, scheduling, arbitration, supervising, controlling or otherwise managing operation of computing system 300, for example, scheduling execution of programs. Memory 320 may be or may include, for example, a Random Access Memory (RAM), a read-only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory, a long term memory, and/or other memory devices. The memory 320 stores executable code 325 that implements the data and operations of the present disclosure, which will be described later herein. Executable code 325 may be any executable code, e.g., an application, a program, a process, task or script. Executable code 325 may be executed by the processor 305 possibly under control of operating system 315.

Storage 330 may be or may include, for example, a hard disk drive, a solid-state drive (SSD), a digital versatile disc (DVD), a universal serial bus (USB) device, and/or other removable and/or fixed device for storing electronic data. Instructions/code and data (e.g., images) may be stored in the storage 330 and may be loaded from the storage 330 into the memory 320, where it may be processed by processor 305.

Input devices 335 may include, for example, a mouse, a keyboard, a touch screen, and/or any other device that can receive an input. Output devices 340 may include one or more monitors, screens, displays, speakers, and/or any other device that can provide an output.

Figure 10:
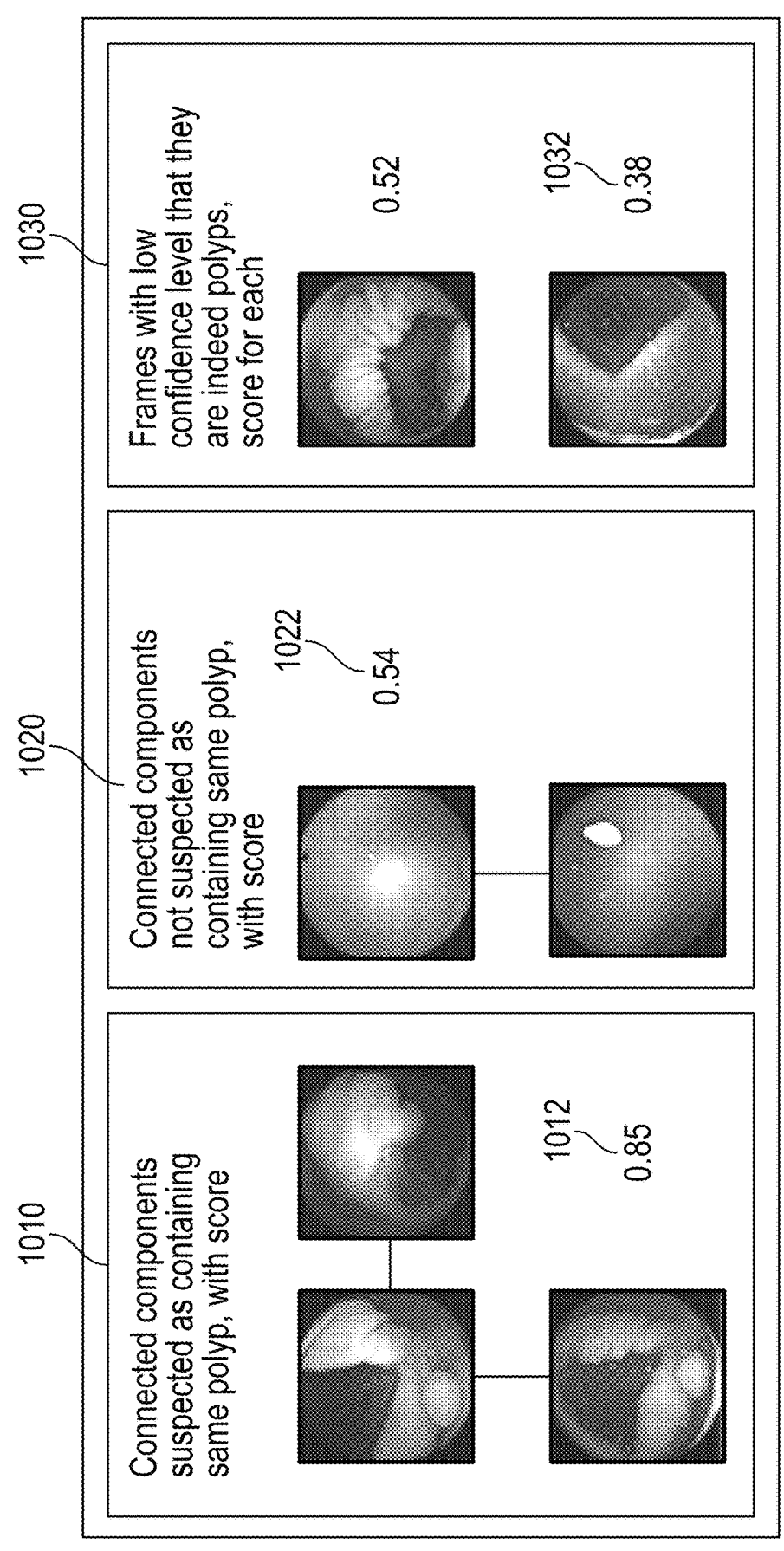
FIG. 10 is a diagram of an exemplary user interface, in accordance with aspects of the disclosure.

Other aspects of the computing system 300 and the capsule system (210, FIG. 2) are described in International Publication No. WO2020236683A1, entitled "Systems and Methods For Capsule Endoscopy Procedure," which is hereby incorporated by reference in its entirety. Generally, the technology of the present disclosure may be utilized by capsule endoscopy systems or methods and may be presented in a user interface, such as the example user interfaces described in International Publication No. WO2020079696, entitled "Systems and Methods for Generating and Displaying a Study of a Stream of In-Vivo Images," which is hereby incorporated by reference herein in its entirety. An example of a user interface is shown in FIG. 10.

The following description may refer to images captured by a capsule endoscopy device. However, the following description may apply to other manners of obtaining images of a GIT or portion of a GIT. The images may be part of a stream of images of the GIT and may be picked out or selected from the stream of GIT images. Colon images may be used merely as an example of the aspects and embodiments described below. The embodiments and aspects described herein also apply to other portions of a GIT, and it is intended that any description related to colon images shall be applicable to images of other portions of a GIT.

Figure 4:
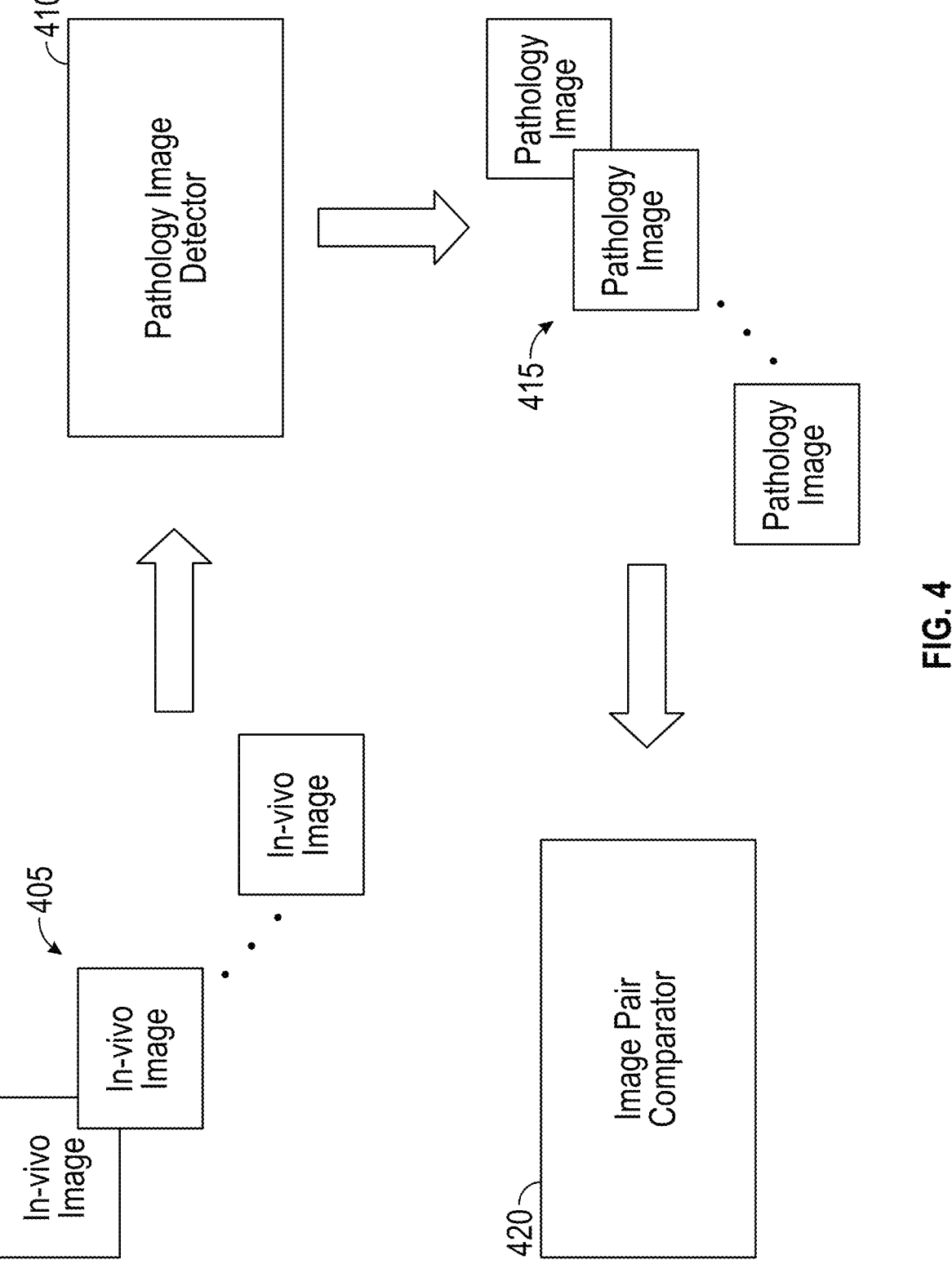
FIG. 4 is a diagram of exemplary image processing, in accordance with aspects of the disclosure.
Figure 5:
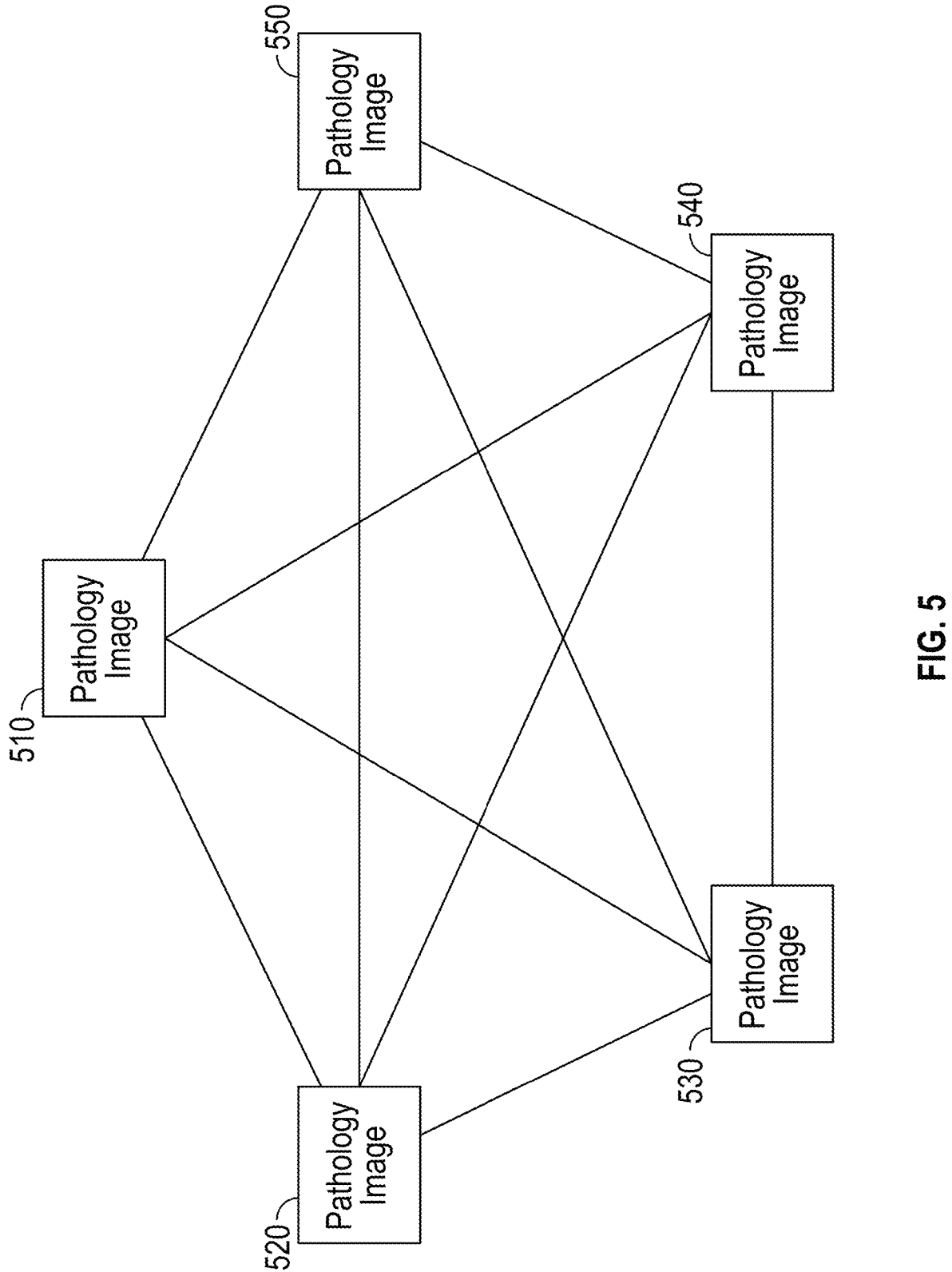
FIG. 5 is a diagram of an exemplary connected graph component, in accordance with aspects of the disclosure.
Figure 7:
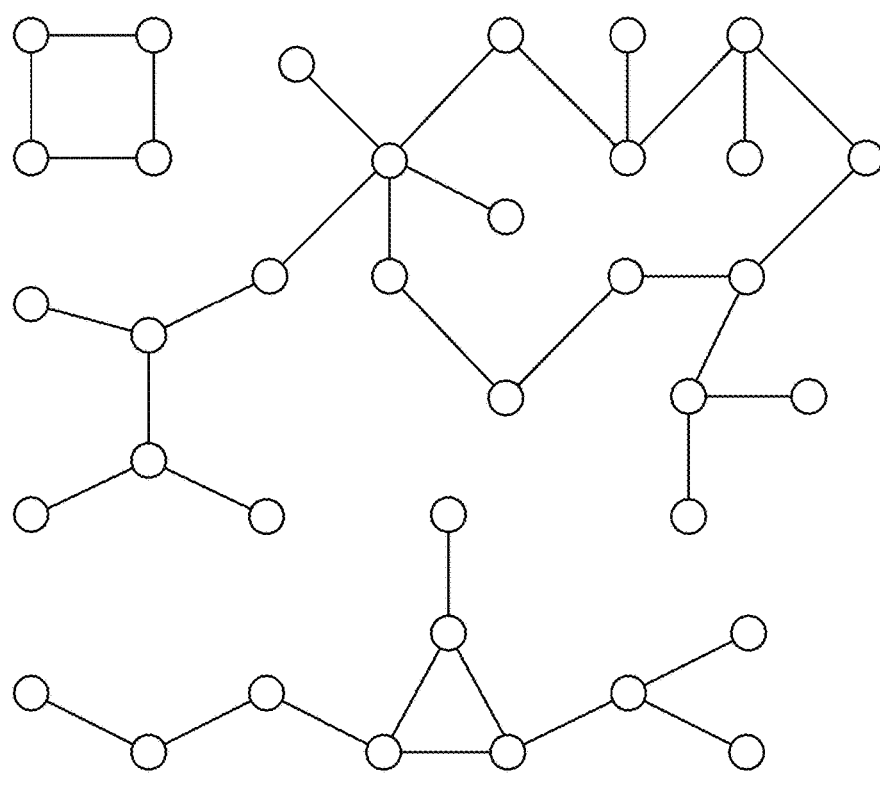
FIG. 7 is a diagram of multiple exemplary connected graph components, in accordance with aspects of the disclosure.
Figure 8:
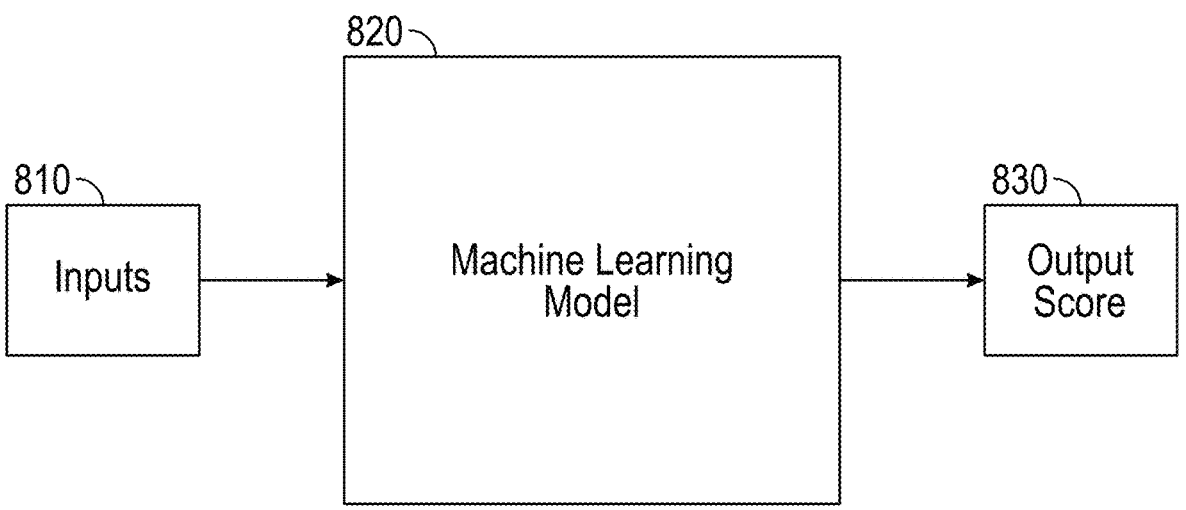
FIG. 8 is a block diagram of an exemplary machine learning model, in accordance with aspects of the disclosure.

In summary, FIG. 4 shows aspects of the present disclosure for processing images of a GIT, FIGS. 5-7 show examples of connecting images based on such processing to form connected graph components, and FIG. 8 shows an example of processing a connected graph component to provide an indication of whether the connected images of the connected graph component contain occurrences of a pathology indicator. The processing of FIGS. 4-8 may be implemented by a computing system, such as by computing system 300 of FIG. 2 and FIG. 3.

Referring to FIG. 4, images of a GIT are shown as in-vivo images 405. The in-vivo images 405 may include all images captured by a capsule endoscope, or by another device, for a particular procedure (e.g., 212, FIG. 2) or may include only a portion of the images captured by the capsule endoscope or another device. Some of the in-vivo images 405 may contain a pathology indicator (such as a polyp) and some of the in-vivo images 405 may not contain the pathology indicator. In accordance with aspects of the present disclosure, a pathology image detector 410 detects which of the in-vivo images 405 may contain a particular pathology indicator. To describe the image processing phases more clearly, the subset of in-vivo images 405 which are designated by the pathology image detector 410 as containing the pathology indicator will be referred to as pathology images 415. Thus, the pathology images 415 are not new or additional images; rather, the pathology images 415 are a subset of the in-vivo images 405.

In various embodiments, the pathology image detector 410 may be implemented using a machine learning model that receives and classifies an image. The machine learning model may be a classical machine learning model, a deep learning neural network model, or a hybrid model. As persons skilled in the art will understand, a classical machine learning model is a model that involves some degree of feature selection to decide what to input to the model, whereas a deep learning neural network may involve, but does not require, feature selection. Examples of a machine learning model used in the pathology image detector 410 include support vector machines or decision trees. As another example, the machine learning model may use a deep learning neural network that receives a frame and a bounding box or a binary mask in an additional channel. The scores from the deep learning neural network can be used (optionally with additional features about the frame) as input to a classical machine learning model (e.g., support vector machine and/or decision tree, etc.). These examples are merely illustrative, and other models are contemplated to be within the scope of the present disclosure.

In operation, the machine learning model that implements the pathology image detector 410 may output a score (not shown) that indicates whether or not an image contains a pathology indicator (e.g., a polyp). The pathology image detector 410 may compare the output score of the machine learning model to a predetermined threshold. Based on the comparison, the pathology image detector 410 may designate the image as containing a pathology indicator or as not containing the pathology indicator. As mentioned above, such a designation for an image is based on image analysis and does not mean and is not intended to mean that the designation is actually true. Rather, the predetermined threshold has a corresponding true positive rate, so the designation has a probability of being true in accordance with the true positive rate.

In various embodiments, the pathology image detector 410 may be configured to detect a particular pathology indicator, such as a polyp. That is, the pathology image detector 410 may receive an input image (e.g., an in-vivo image 405) and may process the input image to either classify it as containing the particular pathology indicator or classify it as not containing the particular pathology indicator. The pathology images 415 include those in-vivo images 405 which are classified by the pathology image detector 410 as containing the particular pathology indicator. These pathology images 415 are passed to the image pair comparator 420, which will be described below.

In various embodiments, the pathology image detector 410 may be configured to detect multiple pathology indicators, such as detecting a polyp or an ulcer, for example. That is, the pathology image detector 410 may receive an input image (e.g., in-vivo image 405) and may process the input image to classify it as containing a first pathology indicator (e.g., polyp), or classify it as containing a second pathology indicator (e.g., ulcer), and so on, or classify it as not containing any of those pathology indicators. In such an implementation, the set of in-vivo images which are indicated as containing the first pathology indicator (e.g., polyp) are passed to an image pair comparator for the first pathology indicator (not shown), and the set of in-vivo images which are indicated as containing the second pathology indicator (e.g., ulcer) are passed on to an image pair comparator for the second pathology indicator (not shown), and so on for other pathology indicators. In various embodiments, a single image pair comparator may be configured to compare images indicated as containing the first pathology indicator and to, separately, compare images indicated as containing the second pathology indicator, and so on for other pathology indicators.

The image pair comparator 420 receives the pathology images 415 and operates to compare each pair of the pathology images 415 to indicate, for each pair, whether or not the two images in the pair contain the same occurrence of a pathology indicator (e.g., the same polyp). The image pair comparator 420 may be implemented in various ways. In various embodiments, the image pair comparator 420 may be implemented using one or more neural networks and using embeddings, as described in International Publication No. WO2022049577A1, which is hereby incorporated by reference herein in its entirety. As described in that publication, the neural network may be trained by a triplet-loss approach using anchor images and positive images that contain the same occurrence of a pathology indicator and using negative images that contain different occurrences of the pathology indicator. Such a trained neural network will be referred to herein as a "triplet-loss network." Accordingly, the image pair comparator 420 may be implemented by one or more triplet-loss networks. In various embodiments, the one or more triplet-loss networks may receive an image as well as a binary mask or a bounding box, as inputs. Such implementation is merely an example, and the image pair comparator 420 may be implemented by other techniques and/or other machine learning models.

Thus, the image pair comparator 420 provides, for each pair of pathology images 415, an indication of whether or not the two images in the pair contain the same occurrence of a pathology indicator (e.g., the same polyp). As mentioned above, the indication does not mean and is not intended to mean that the two images in a pair actually contain the same occurrence or actually contain different occurrences of a pathology indicator. Rather, the indication is based on image processing and may or may not be actually true.

In various embodiments, for each image pair, such an indication may be referred to herein as a "distance" between the two images in the pair. A sufficiently small distance (e.g., below a predetermined threshold) may indicate that the two images contain the same occurrence of a pathology indicator (e.g., the same polyp). A distance greater than the predetermined threshold may indicate that the two images contain different occurrences of a pathology indicator (e.g., distinct polyps). As described in connection with FIGS. 5-7 below, the indicators/distances provided by the image pair comparator 420 may be used to form one or more connections between the pathology images 415 and, thereby, form one or more connected graph components.

FIG. 5 shows an example of pathology images that includes five pathology images 510-550. In accordance with aspects of the present disclosure, a connection is formed between two pathology images when the indicator/distance provided by the image pair comparator 420 (FIG. 4) indicates that the two pathology images contain the same occurrence of a pathology indicator. In the example of FIG. 5, every pathology image in FIG. 5 is connected to every other image, which means that every pair of the five pathology images 510-550 have indicators/distances indicating they contain the same occurrence of a pathology indicator. Treating each pathology image as a node and each connection as an edge, the nodes and edges in FIG. 5 form a single connected graph component.

FIG. 6 shows an example where the indicator/distance provided by the image pair comparator 420 (FIG. 4) connects pathology images 510-530 to each other but not to pathology images 540 and 550. But pathology images 540 and 550 are connected to each other. Treating each pathology image as a node and each connection as an edge, the nodes and edges in FIG. 6 form two separate connected graph components. The connected graph components of FIG. 6 may be formed in two ways. In a first way, all nodes are initially connected with each other by edges, and any image pair which is indicated by the image pair comparator 420 (FIG. 4) as not containing the same occurrence of a pathology indicator can have its edge removed. In the second way, all nodes are initially unconnected, and any image pair which is indicated by the image pair comparator 420 as containing the same occurrence of a pathology indicator can have its edge added. Both ways of forming a connected graph component, or a combination of the two ways, are contemplated to be within the scope of the present disclosure.

Generally, any number of pathology images 415 (FIG. 4) may be processed by the image pair comparator 420 (FIG. 4) to form pairwise connections, and any number, shape, or size of connected graph components may result from those connections. FIG. 7 shows examples of various connected graph components of various shapes and sizes that may result from the processing of FIG. 4. Such examples are merely illustrative, and other numbers, shapes, and sizes of connected graph components are within the scope of the present disclosure.

Accordingly, described above are techniques for processing in-vivo images to form connected graph components that include two or more pathology images as graph nodes. In a particular connected graph component, the interconnection of pathology images through edges suggests that all of the pathology images in a connected graph component contain the same occurrence of a pathology indicator. However, because the edges in the connected graph component result from pairwise determinations, there are situations where the pathology images in a connected graph component may not all contain the same occurrence of a pathology indicator.

In accordance with aspects of the present disclosure, a machine learning model may be used to process a connected graph component to provide an indication of whether or not all pathology images in a connected graph component contain the same occurrence of a pathology indicator. FIG. 8 shows a block diagram of a machine learning model 820 that receives inputs 810 (that are based on a connected graph component) and provides an output score 820 indicative of whether or not all pathology images in the connected graph component contain the same occurrence of a pathology indicator. When there are multiple connected graph components, such as in FIG. 7, the machine learning model 820 processes the connected graph components one at a time.

In accordance with aspects of the present disclosure, the machine learning model 820 may be a classical machine learning model or a deep learning neural network or a hybrid model. Examples of classical machine learning models that may be used include support vector machines or decision trees, among others. As persons skilled in the art will understand, a support vector machine may provide an output score 830 based on a distance between the input vector 810 and a decision boundary of the support vector machine, and a decision tree may provide an output score 830 based on the percentage of training vectors classified in accordance with a decision node. An output score 830 may be provided by other types of classical machine learning models, as well. Persons skilled in the art will understand how to implement and train classical machine learning models and how to implement and train deep learning neural networks.

In accordance with aspects of the present disclosure, the inputs 810 to the machine learning model 820 include graph characteristics of the connected graph component. The machine learning model 820 processes a connected graph component by receiving the graph characteristics (and optionally other data) as inputs 810 and by applying a learned model to the inputs to provide the output score 830. The graph characteristics of a connected graph component may include, for example, number of nodes in the connected graph component, number of edges in the connected graph component, ratio of nodes to edges in the connected graph component, ratio of edges to nodes in the connected graph component, and/or shape/structure of the connected graph component, among other things. In various embodiments, the graph characteristics may include one or more metrics that are based on the scores that the pathology image detector 410 (FIG. 4) provides for the pathology images 415. In various embodiments, the graph characteristics may include one or more metrics that are based on the indicators/ distances that the image pair comparator 420 (FIG. 4) provides for the edges connecting the pathology images 415. Such metrics may be or may be based on, for example, maximum, minimum, sum, median, mean, standard deviation, and/or other quantities. Such graph characteristics of a connected graph component may be provided to the machine learning model 820 as inputs 810.

Based on receiving the graph characteristics as inputs 810 (and optionally based on other additional inputs), the machine learning model 820 may determine an output score 830 that indicates whether or not all pathology images in the connected graph component contain the same occurrence of a pathology indicator. In various embodiments, a sufficiently high output score 830 (e.g., above a predetermined threshold) may indicate that all pathology images or part of the pathology images in the connected graph component contain the same occurrence of a pathology indicator. An output score 830 that is sufficient low (e.g., below a predetermined threshold), in contrast, may indicate that the pathology images in the connected graph component contain different occurrences of a pathology indicator or no pathologies at all. In various embodiments, multiple thresholds may be used or predetermined output score range or ranges may be used. The predetermined threshold(s) or predetermined range(s) may be selected empirically. The output score 830 for a connected graph component may be associated with the pathology images in the connected graph component. A user interface for presenting the pathology images of a connected graph component and for presenting an associated output score will be described in connection with FIG. 10.

Referring now to FIG. 9, there is shown a flow diagram of an operation for processing in-vivo images in accordance with aspects of the present disclosure. The operations of FIG. 9 may be implemented by a computing system, such as computing system 300 of FIG. 2 and FIG. 3, and may be implemented using the technology described in connection with FIG. 4 and FIG. 8.

At block 910, the operation involves accessing a plurality of in-vivo images of at least a portion of a gastrointestinal tract. The plurality of in-vivo images may already be designated as including a pathology indicator (e.g., polyp) and may include the pathology images 415 of FIG. 4. Accordingly, block 910 occurs after the pathology image detector 410 (FIG. 4) has identified the pathology images 415.

At block 920, the operation involves forming a connected graph component based on the plurality of in-vivo images (e.g., pathology images 415). The connected graph component may be one of the connected graph components shown in FIGS. 5-7, for example. The connected graph component includes two or more images from the plurality of in-vivo images (e.g., pathology images 415) that are connected based on one or more indications that the two or more images contain the same occurrence of the pathology indicator (e.g., the same polyp). As described in connection with FIG. 4, the connected graph component may be formed based on indications/distances provided by the image pair comparator 420. As described above, a connected graph component may be formed in two ways. In a first way, all nodes are initially connected with each other by edges, and any image pair which is indicated by the image pair comparator 420 (FIG. 4) as not containing the same occurrence of a pathology indicator can have its edge removed. In the second way, all nodes are initially unconnected, and any image pair which is indicated by the image pair comparator 420 as containing the same occurrence of a pathology indicator can have its edge added. Both ways of forming a connected graph component, or a hybrid of the two ways, are contemplated to be within the scope of the present disclosure.

At block 930, the operation involves processing the connected graph component with a machine learning model to provide a score that indicates whether or not the two or more images of the connected graph component all contain the same occurrence of the pathology indicator. As mentioned above, the edges in the connected graph component result from pairwise determinations, so there are situations where the pathology images in a connected graph component may not all contain the same occurrence of a pathology indicator. Thus, the operation at block 930 operates to determine whether or not all images in a connected graph component contain the same occurrence of a pathology indicator. The machine learning model and the score of block 930 may be implemented by the machine learning model 820 and output score 830 described in connection with FIG. 8. For example, the machine learning model may receive input values that include graph characteristics of a connected graph component, such as number of nodes, number of edges, ratio of nodes to edges, ratio of edges to nodes, and/or shape/structure of the connected graph component, among other things.

At block 940, the operation involves associating the score, which is indicative of whether or not all images in the connected graph component contain the same occurrence of a pathology indicator, with the two or more images of the connected graph component, for presentation to a reviewer of those images.

The operation of FIG. 9 is exemplary and additional blocks may be added, or different blocks may be substituted for those illustrated, without departing from the scope of the present disclosure.

FIG. 10 shows an exemplary user interface for presenting images of a connected graph component. The user interface may be served or otherwise communicated by a computing system (e.g., computing system 300, FIG. 2) to a device of a reviewer who is reviewing the images.

In accordance with aspects of the present disclosure, a first portion 1010 of the user interface can present connected graph components which have a sufficiently high output score (e.g., 830, FIG. 8) (e.g., above a predetermined threshold) to indicate that all images of the connected graph component contain the same occurrence of a pathology indicator (e.g., the same polyp). In various embodiments, the portion 1010 may include explanatory text, and the associated output score 1012 may be displayed in such portion 1010 of the user interface to provide the reviewer with information about the determination. A second portion 1020 of the user interface can present connected graph components which have output score (e.g., 830, FIG. 8) indicating that the images of the connected graph component contain different occurrences of a pathology indicator (e.g., distinct polyps). In various embodiments, the portion 1020 may include explanatory text, and the associated output score 1022 may be displayed in such portion 1020 of the user interface to provide the reviewer with information about the determination. Optionally, a third portion 1030 of the user interface may present images that are not designated by the pathology image detector 410 (FIG. 4) as containing a pathology indicator. In various embodiments, the scores 1032 provided by the pathology image detector 410 for such images may be displayed in the third portion 1030.

In the first and second portions 1010, 1020, the user interface may display the edges connecting images. In various embodiments, a user may select an edge to view a next image connected by the selected edge. In this way, a reviewer may traverse a connected graph component using the user interface.

FIG. 10 is exemplary, and variations are contemplated to be within the scope of the present disclosure. For example, in various embodiments, the first, second, and third portions 1010-1030 may not all be simultaneously displayed. For example, only one portion or only two portions may be displayed by the user interface, and a user may direct the user interface to display another portion using user interface elements, such as tabs, menus, and buttons, among others (not shown). Such and other variations are contemplated to be within the scope of the present disclosure.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in various embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

The systems, devices, and/or servers described herein may utilize one or more processors to receive various information and transform the received information to generate an output. The processors may include any type of computing device, computational circuit, or any type of controller or processing circuit capable of executing a series of instructions that are stored in a memory. The processor may include multiple processors and/or multicore central processing units (CPUs) and may include any type of device, such as a microprocessor, graphics processing unit (GPU), digital signal processor, microcontroller, programmable logic device (PLD), field programmable gate array (FPGA), or the like. The processor may also include a memory to store data and/or instructions that, when executed by the one or more processors, causes the one or more processors to perform one or more methods and/or algorithms.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, Python, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed:

1. A system for analyzing images, comprising:
at least one processor; and
at least one memory storing instructions which, when executed by the at least one processor, cause the system to:
   access a plurality of in-vivo images of at least a portion of a gastrointestinal tract, the plurality of in-vivo images designated as including a pathology indicator,
   form a connected graph component based on the plurality of in-vivo images, the connected graph component comprising at least two images of the plurality of in-vivo images connected based on at least one indication that the at least two images contain a same occurrence of the pathology indicator,
   process the connected graph component with a machine learning model to provide a score indicative of whether the at least two images contain the same occurrence of the pathology indicator, and
   associate the score with the at least two images for a presentation to a reviewer of the at least two images.

2. The system of claim 1, wherein in forming the connected graph component based on the plurality of in-vivo images, the instructions, when executed by the at least one processor, cause the system to:
   for each image pair of the plurality of in-vivo images:
      analyze whether both images of the respective image pair contain a same occurrence of the pathology indicator, and
      based on the analysis indicating that both images of the respective image pair contain the same occurrence of the pathology indicator, designate both images of the respective image pair as graph nodes and connect the graph nodes by an edge; and
   select a group of graph nodes which are connected by one or more edges as the connected graph component.

3. The system of claim 2, wherein in analyzing whether both images of the respective image pair contain the same occurrence of the pathology indicator, the instructions, when executed by the at least one processor, cause the system to:

process both images of the respective image pair by a triplet-loss network to provide an output score; and provide an indication of whether both images of the respective image pair contain the same occurrence of the pathology indicator based on comparing the output score to a predetermined score threshold.

4. The system of claim 1, wherein the instructions, when executed by the at least one processor, further cause the system to:

determine at least one graph characteristic of the connected graph component, wherein processing the connected graph component with the machine learning model comprises inputting the at least one graph characteristic to the machine learning model.

5. The system of claim 4, wherein the at least one graph characteristic comprises at least one of: number of nodes of the connected graph component, number of edges of the connected graph component, ratio of nodes to edges in the connected graph component, or ratio of edges to nodes in the connected graph component.

6. The system of claim 1, wherein the instructions, when executed by the at least one processor, further cause the system to:

communicate a user interface to a device of the reviewer, the user interface comprising a presentation of the at least two images and of the score associated with the at least two images.

7. The system of claim 6, wherein the user interface further comprises:

based on a value of the score associated with the at least two images, one of:

an indication that the at least two images may contain the same occurrence of the pathology indicator, or an indication that the at least two images may contain different occurrences of the pathology indicator.

8. A method for analyzing images, comprising:

accessing a plurality of in-vivo images of at least a portion of a gastrointestinal tract, the plurality of in-vivo images designated as including a pathology indicator;

forming a connected graph component based on the plurality of in-vivo images, the connected graph component comprising at least two images of the plurality of in-vivo images connected based on at least one indication that the at least two images contain a same occurrence of the pathology indicator;

processing the connected graph component with a machine learning model to provide a score indicative of whether the at least two images contain the same occurrence of the pathology indicator; and associating the score with the at least two images for a presentation to a reviewer of the at least two images.

9. The method of claim 8, wherein forming the connected graph component based on the plurality of in-vivo images comprises:

for each image pair of the plurality of in-vivo images:

analyzing whether both images of the respective image pair contain a same occurrence of the pathology indicator, and based on the analysis indicating that both images of the respective image pair contain the same occurrence of the pathology indicator, designating both images of the respective image pair as graph nodes and connecting the graph nodes by an edge; and selecting a group of graph nodes which are connected by one or more edges as the connected graph component.

10. The method of claim 9, wherein analyzing whether both images of the respective image pair contain the same occurrence of the pathology indicator comprises:

processing both images of the respective image pair by a triplet-loss network to provide an output score; and providing an indication of whether both images of the respective image pair contain the same occurrence of the pathology indicator based on comparing the output score to a predetermined score threshold.

11. The method of claim 8, further comprising:

determining at least one graph characteristic of the connected graph component, wherein processing the connected graph component with the machine learning model comprises inputting the at least one graph characteristic to the machine learning model.

12. The method of claim 11, wherein the at least one graph characteristic comprises at least one of: number of nodes of the connected graph component, number of edges of the connected graph component, ratio of nodes to edges in the connected graph component, or ratio of edges to nodes in the connected graph component.

13. The method of claim 8, further comprising:

communicating a user interface to a device of the reviewer, the user interface comprising a presentation of the at least two images and of the score associated with the at least two images.

14. The method of claim 13, wherein the user interface further comprises:

based on a value of the score associated with the at least two images, one of:

an indication that the at least two images may contain the same occurrence of the pathology indicator, or an indication that the at least two images may contain different occurrences of the pathology indicator.

15. A non-transitory processor-readable medium storing instructions which, when executed by at least one processor of a system, cause the system to:

access a plurality of in-vivo images of at least a portion of a gastrointestinal tract, the plurality of in-vivo images designated as containing a pathology indicator, form a connected graph component based on the plurality of in-vivo images, the connected graph component comprising at least two images of the plurality of in-vivo images connected based on at least one indication that the at least two images contain a same occurrence of the pathology indicator, process the connected graph component with a machine learning model to provide a score indicative of whether the at least two images contain the same occurrence of the pathology indicator, and associate the score with the at least two images for a presentation to a reviewer of the at least two images.

16. The non-transitory processor-readable medium of claim 15, wherein in forming the connected graph component based on the plurality of in-vivo images, the instructions, when executed by the at least one processor, cause the system to:

for each image pair of the plurality of in-vivo images:

analyze whether both images of the respective image pair contain a same occurrence of the pathology indicator, and based on the analysis indicating that both images of the respective image pair contain the same occurrence of the pathology indicator, designate both images of the respective image pair as graph nodes and connect the graph nodes by an edge; and select a group of graph nodes which are connected by one or more edges as the connected graph component.

17. The non-transitory processor-readable medium of claim 16, wherein in analyzing whether both images of the respective image pair contain the same occurrence of the pathology indicator, the instructions, when executed by the at least one processor, cause the system to:

process both images of the respective image pair by a triplet-loss network to provide an output score; and provide an indication of whether both images of the respective image pair contain the same occurrence of the pathology indicator based on comparing the output score to a predetermined score threshold.

18. The non-transitory processor-readable medium of claim 15, wherein the instructions, when executed by the at least one processor, further cause the system to:

determine at least one graph characteristic of the connected graph component, wherein processing the connected graph component with the machine learning model comprises inputting the at least one graph characteristic to the machine learning model.

19. The non-transitory processor-readable medium of claim 18, wherein the at least one graph characteristic comprises at least one of: number of nodes of the connected graph component, number of edges of the connected graph component, ratio of nodes to edges in the connected graph component, or ratio of edges to nodes in the connected graph component.

20. The non-transitory processor-readable medium of claim 15, wherein the instructions, when executed by the at least one processor, further cause the system to:

communicate a user interface to a device of the reviewer, the user interface comprising a presentation of the at least two images and of the score associated with the at least two images.

* * * * *